(12) United States Patent
Lin et al.

(10) Patent No.: US 10,563,205 B2
(45) Date of Patent: Feb. 18, 2020

(54) NUCLEIC ACID APTAMER AS1411 MODIFIED DNA TETRAHEDRON AND PREPARATION METHOD THEREOF

(71) Applicant: Sichuan University, Chengdu (CN)

(72) Inventors: Yunfeng Lin, Chengdu (CN); Qianshun Li, Chengdu (CN); Xiaoxiao Cai, Chengdu (CN); Shiyu Lin, Ruian (CN); Xiaoru Shao, Jining (CN)

(73) Assignee: SICHUAN UNIVERSITY, Chengdu (CN)

( * ) Notice: Subject to any disclaimer, the term of this patent is extended or adjusted under 35 U.S.C. 154(b) by 110 days.

(21) Appl. No.: 15/744,849

(22) PCT Filed: Nov. 30, 2016

(86) PCT No.: PCT/CN2016/107816
§ 371 (c)(1),
(2) Date: Jan. 15, 2018

(87) PCT Pub. No.: WO2018/082143
PCT Pub. Date: May 11, 2018

(65) Prior Publication Data
US 2019/0048347 A1 Feb. 14, 2019

(30) Foreign Application Priority Data
Nov. 2, 2016 (CN) .......................... 2016 1 0942153

(51) Int. Cl.
*C12N 15/115* (2010.01)
*G01N 21/33* (2006.01)
*A61K 47/26* (2006.01)
*A61K 47/54* (2017.01)
*C12N 15/11* (2006.01)

(52) U.S. Cl.
CPC ............ *C12N 15/115* (2013.01); *A61K 47/26* (2013.01); *A61K 47/549* (2017.08); *C12N 15/11* (2013.01); *G01N 21/33* (2013.01); *C12N 2310/16* (2013.01); *C12N 2310/18* (2013.01); *C12N 2310/30* (2013.01); *C12N 2310/3519* (2013.01); *C12N 2330/30* (2013.01)

(58) Field of Classification Search
CPC .............. A61K 31/711; A61K 2300/00; A61K 47/6929; C12N 15/115; C12N 2310/16; C12N 2320/32
USPC ...... 424/9.1; 435/6.1, 91.1, 91.31, 455, 458; 514/44; 536/23.1, 24.5
See application file for complete search history.

(56) References Cited

FOREIGN PATENT DOCUMENTS

| CN | 103301481 A | 9/2013 |
|---|---|---|
| CN | 104399969 A | 3/2015 |
| CN | 105366730 A | 3/2016 |
| WO | 0196541 A2 | 12/2001 |
| WO | 2008125116 A2 | 10/2008 |

OTHER PUBLICATIONS

Xu et al, Nanoscale Res. Letters, vol. 11, p. 437, pp. 1-8. (Year: 2016).*
Li et al, ACS Nano, vol. 5, No. 11, pp. 8783-8789. (Year: 2011).*

\* cited by examiner

*Primary Examiner* — Jane J Zara
(74) *Attorney, Agent, or Firm* — Gokalp Bayramoglu

(57) ABSTRACT

This invention discloses a nucleic acid aptamer AS1411 modified DNA tetrahedron. The preparation method includes the steps of (1) binding an AS1411 sequence to the 5' terminal of any DNA single-strand in a DNA tetrahedron, synthesizing the DNA, dissolving obtained DNA powder with ddH$_2$O; (2) measuring an absorbance of the DNA and then calculating a total volume of the four single strands; (3) pipetting the DNA obtained in step (1) according to the calculation results in step (2), mixing the DNA with a TM buffer, mixing the mixture uniformly with vortex vibration, and performing a PCR progress. The preparation method is simple. The produced product can effectively solve the problem that the unmodified DNA tetrahedron cannot enter the nucleus and the problem that the AS1411 cannot carry drugs directly.

8 Claims, 1 Drawing Sheet
Specification includes a Sequence Listing.

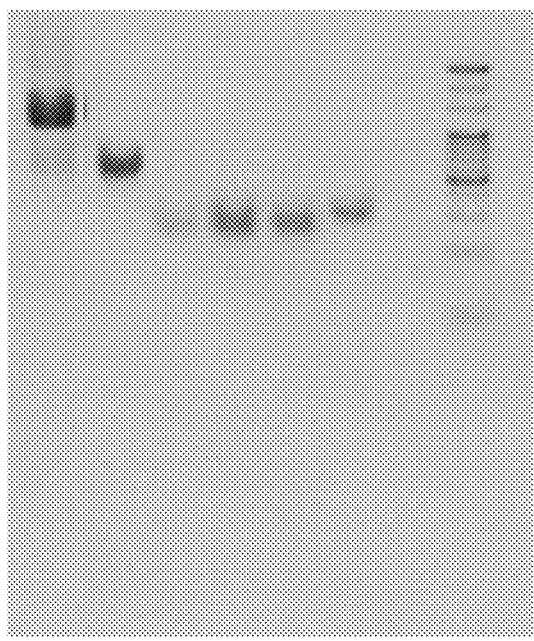

NUCLEIC ACID APTAMER AS1411 MODIFIED DNA TETRAHEDRON AND PREPARATION METHOD THEREOF

CROSS REFERENCE TO RELATED APPLICATIONS

This application is the national phase entry of International Application No. PCT/CN2016/107816, filed on Nov. 30, 2016, which is based upon and claims priority to Chinese Patent Application No. CN201610942153.7, filed on Nov. 2, 2016, the entire contents of which are incorporated herein by reference.

TECHNICAL FIELD

The invention relates to the field of DNA tetrahedron, specifically to a nucleic acid aptamer AS1411 modified DNA tetrahedron and the preparation method thereof.

BACKGROUND

At present, the DNA tetrahedron has a great potential in the fields of medicine delivery, cancer treatment, etc., due to DNA tetrahedron's good biocompatibility, good stability and modifiability, and relatively simple synthesis method. The DNA tetrahedron can be used as a nano drug delivery with good biocompatibility. Compared to most traditional nano materials, DNA tetrahedron can be transported to cell lysosomes through caveolin-mediated endocytosis pathway mechanism, microtubule-dependent pathway, and can maintain the structure in cells for a relatively long time. DNA tetrahedron can successfully transport the immunostimulant CpG into cells to take effect. However, as with the individual DNA tetrahedron, the carried drugs also enter the lysosomes, which lead to the rapid degradation of drugs by lysosomes.

Nucleic acid aptamer AS1411 is a DNA single-strand that can specifically bind to pyrenin. Pyrenin is highly expressed on nucleus and the surface of the tumor cell membrane. Moreover, the AS1411 can enter the nucleus via the intracellular shuttle effect of the pyrenin. Meanwhile, the AS1411 can inhibit the DNA replication, so as to force the cells to stay in S phase, thereby inhibiting cell proliferation. AS1411 interferes with the binding of pyrenin and bcl-2 so as to promote apoptosis of cells. Hence, AS1411 has a great prospect in cancer diagnosis and treatment.

However, using the AS1411 nucleic acid aptamer to modify the DNA tetrahedron has not been reported yet.

SUMMARY OF THE INVENTION

In view of the above deficiencies in the prior art, this invention provides a nucleic acid aptamer AS1411 modified DNA tetrahedron and preparation method thereof. The present invention can effectively solve the problem that the unmodified DNA tetrahedron cannot enter the nucleus and the problem that the AS1411 cannot carry drugs directly.

In order to achieve the above objective, the technical solutions of this invention to solve the technical problem are as below:

A method for preparing a nucleic acid aptamer AS1411 modified DNA tetrahedron, including the following steps:

(1) binding an AS1411 sequence to any DNA single-strand of a DNA tetrahedron at the 5' terminal of the DNA, synthesizing the DNA, centrifuging the obtained DNA powder at a high speed to ensure that the DNA powder aggregates at a bottom of the tube, dissolving the obtained DNA powder with ddH$_2$O, storing at the condition of 4° C.;

(2) measuring an absorbance of the DNA at wavelengths of 260 nm and 330 nm by ultraviolet quantitation method, then calculating the volume of each single strand in a 100 μl, 1 μM system according to the following formula:

$V=100/[(A_{260}-A_{330})\times10^5(15.2\times$a number of adenine in a single strand$+7.4\times$a number of cytosine in the single strand$+11.4\times$a number of guanine in the single strand$+8.3\times$a number of thymine in the single strand)], calculating a total volume of the four single strands according to the above calculation results;

(3) pipetting the DNA obtained in step (1) according to the calculated total volume in step (2), mixing the DNA with a TM buffer to obtain a mixture, mixing the mixture uniformly with vortex vibration, and putting the mixture into a PCR apparatus; raising the temperature to 95° C. quickly and maintaining for 10 min; and then cooling down to 4° C. and maintaining for 20 min, and finally storing at −20° C. to obtain the nucleic acid aptamer AS1411 modified DNA tetrahedron.

Further, in step (1), 1 nmol DNA is dissolved in 10 μL ddH$_2$O.

Further, the TM buffer in step (3) having a pH value of 8.0 includes 5-10 mM Tris-HCl and 5-50 mM MgCl$_2$.

Further, the TM buffer in step (3) having a pH value of 8.0 includes 10 mM Tris-HCl and 50 mM MgCl$_2$.

The sequences of four DNA single strands of the DNA tetrahedron respectively are as below:

S1:
(SEQ ID NO: 1)
5'-ATTTATCACCCGCCATAGTAGACGTATCACCAGGCAGTTGAGACGA

ACATTCCTAAGTCTGAA-3';

S2:
(SEQ ID NO: 2)
5'-ACATGCGAGGGTCCAATACCGACGATTACAGCTTGCTACACGATTC

AGACTTAGGAATGTTCG-3';

S3:
(SEQ ID NO: 3)
5'-ACTACTATGGCGGGTGATAAAACGTGTAGCAAGCTGTAATCGACGG

GAAGAGCATGCCCATCC-3'

S4:
(SEQ ID NO: 4)
5'-ACGGTATTGGACCCTCGCATGACTCAACTGCCTGGTGATACGAGGA

TGGGCATGCTCTTCCCG-3'.

The AS1411 has a sequence of:

(SEQ ID NO: 5)
5'-GGTGGTGGTGGTTGTGGTGGTGGTGGT-3'.

The AS1411 can bind to any single strand of the DNA tetrahedron at the 5' terminal of the DNA. The sequence thereof after binding is:

S1-AS1411:
(SEQ ID NO: 6)
5'-GGTGGTGGTGGTTGTGGTGGTGGTGGT-ATTTATCACCCGCCATA

GTAGACGTATCACCAGGCAGTTGAGACGAACATTCCTAAGTCTGAA-3';

-continued

S2-AS1411:
(SEQ ID NO: 7)
5'-GGTGGTGGTGGTTGTGGTGGTGGTGGT-ACATGCGAGGGTCCAATA

CCGACGATTACAGCTTGCTACACGATTCAGACTTAGGAATGTTCG-3';

S3-AS1411:
(SEQ ID NO: 8)
5'-GGTGGTGGTGGTTGTGGTGGTGGTGGT-ACTACTATGGCGGGTGA

TAAAACGTGTAGCAAGCTGTAATCGACGGGAAGAGCATGCCCATCC-3';

S4-AS1411:
(SEQ ID NO: 9)
5'-GGTGGTGGTGGTTGTGGTGGTGGTGGT-ACGGTATTGGACCCTCGC

ATGACTCAACTGCCTGGTGATACGAGGATGGGCATGCTCTTCCCG-3'.

The verification of the nucleic acid aptamer AS1411 modified DNA tetrahedron: a polyacrylamide gel electrophoresis (PAGE) method is used. That is, diluting each of the unmodified single strand of the DNA tetrahedron by 100-fold, taking 5 µL of the dilution to mix with 1 µL of 6×loading buffer, taking 5 µL of the modified DNA tetrahedron to mix with 1 µL of 6×loading buffer, adding the solutions into a prepared gel (the ingredients of the gel: ultrapure water 4.2 mL, 40% acrylamide 1.2 mL, 10×TAE 0.6 mL, 10% APS 60 µL and TEMED 6 µL) respectively, adding a 20 bp marker in a side of the gel as a control, conducting electrophoresis in a 1×TAE buffer at a constant voltage of 100V for 80 minutes. Adding 50 ml ddH$_2$O and 5 µL Gel-red to a box without light, mixing uniformly, putting the gel into the box, shaking in a shaker for 15-20 minutes, and taking a picture via a gel imaging system.

The nucleic acid aptamer AS1411 modified DNA tetrahedron provided by the present invention has the following beneficial effects:

(1) The traditional DNA tetrahedron can only enter the cell but not the nucleus, and the AS1411 cannot deliver drugs directly. The present invention modifies the DNA tetrahedron with the nucleic acid aptamer AS1411 to form a drug carrier with high efficiency.

(2) The synthesis method is simple. The nucleic acid aptamer AS1411 can mediate the DNA tetrahedron into the nucleus to effectively improve the efficiency of drug delivery. The traditional DNA tetrahedron cannot enter the nucleus. Most of the cancer treating drugs inhibit biological behaviors of the tumor cells including proliferation and migration through binding to DNA, while most of the DNA exists in the nucleus. Thus, the AS1411 improves the efficiency of drug delivery by mediating the DNA tetrahedron onto the nucleus. Furthermore, the AS1411 itself can also inhibit the proliferation of tumor cells, and it can achieve double anti-tumor effect after delivering drugs.

(3) AS1411 can bind to pyrenin on the surface of tumor cell membrane in a targeted manner, whereas there is no pyrenin receptor on the surface of normal cells membrane. Therefore, the tetrahedron modified with AS1411 can deliver antitumor drugs in a targeted manner, such that the drug entering the tumor cells is significantly more than that entering the normal cells. Thus, the tumor cells can be treated well. Meanwhile, the damage to normal cells caused by the drug can be further reduced.

BRIEF DESCRIPTION OF THE DRAWINGS

FIGURE is an electrophoretogram of the nucleic acid aptamer AS1411 modified DNA tetrahedrons; wherein from right to left, the brands respectively are: marker, single strand S1, single strand S2, single strand S3, single strand S4, the nucleic acid aptamer AS1411 modified single strand S4, and the nucleic acid aptamer AS1411 modified DNA tetrahedron (Embodiment 4).

DETAILED DESCRIPTION OF THE INVENTION

Embodiment 1

A method for preparing a nucleic acid aptamer AS1411 modified DNA tetrahedron includes the following steps:

(1) binding an AS1411 sequence to S1 of the DNA tetrahedron at the 5' terminal, synthesizing the DNA using an automatic DNA synthesizer to obtain a DNA powder, centrifuging the obtained DNA powder at a high speed to ensure that the DNA powder aggregates at a bottom of the tube, dissolving the obtained DNA powder with ddH$_2$O (1 nmol DNA is dissolved in 10 µL ddH$_2$O), storing at the condition of 4° C.; wherein the AS1411 sequence is shown in SEQ ID NO: 5, and S1 has a sequence of SEQ ID NO: 1;

(2) measuring an absorbance of the DNA at wavelengths of 260 nm and 330 nm by ultraviolet quantitation method, then calculating the volume of each single strand in a 100 µL, 1 µM system according to the following formula:

$V=100/[(A_{260}-A_{330})\times10^5/(15.2\times$a number of adenine in a single strand$+7.4\times$a number of cytosine in the single strand$+11.4\times$a number of guanine in the single strand$+8.3\times$a number of thymine in the single strand$)]$, calculating a total volume of the four single strands according to the above calculation results;

(3) pipetting the DNA obtained in step (1) according to the calculated total volume in step (2), mixing the DNA with a TM buffer (10 mM Tris-HCl, 50 mM MgCl$_2$, pH 8.0) to obtain a mixture, mixing the mixture uniformly with vortex vibration, and putting the mixture into a PCR apparatus; raising the temperature to 95 quickly and maintaining for 10 min; and then cooling down to 4° C. and maintaining for 20 min, and finally storing at −20° C. to obtain the nucleic acid aptamer AS1411 modified DNA tetrahedron.

Embodiment 2

A method for preparing a nucleic acid aptamer AS1411 modified DNA tetrahedron includes the following steps:

(1) binding an AS1411 sequence to S2 of the DNA tetrahedron at the 5' terminal, synthesizing the DNA using an automatic DNA synthesizer to obtain a DNA powder, centrifuging the obtained DNA powder at a high speed to ensure that the DNA powder aggregates at a bottom of the tube, dissolving the obtained DNA powder with ddH$_2$O (1 nmol DNA is dissolved in 10 µL ddH$_2$O), storing at the condition of 4° C.; wherein the AS1411 sequence is shown in SEQ ID NO: 5, and S2 has a sequence of SEQ ID NO: 2;

(2) measuring an absorbance of the DNA at wavelengths of 260 nm and 330 nm by ultraviolet quantitation method, then calculating the volume of each single strand in a 100 µL, 1 µM system according to the following formula:

$V=100/[(A_{260}-A_{330})\times10^5/(15.2\times$a number of adenine in a single strand$+7.4\times$a number of cytosine in the single strand$+11.4\times$a number of guanine in the single strand$+8.3\times$a number of thymine in the single strand$)]$, calculating a total volume of the four single strands according to the above calculation results;

(3) pipetting the DNA obtained in step (1) according to the calculated total volume in step (2), mixing the DNA with a TM buffer (10 mM Tris-HCl, 50 mM $MgCl_2$, pH 8.0) to obtain a mixture, mixing the mixture uniformly with vortex vibration, and putting the mixture into a PCR apparatus; raising the temperature to 95° C. quickly and maintaining for 10 min; and then cooling down to 4° C. and maintaining for 20 min, and finally storing at −20° C. to obtain the nucleic acid aptamer AS1411 modified DNA tetrahedron.

Embodiment 3

A method for preparing a nucleic acid aptamer AS1411 modified DNA tetrahedron includes the following steps:

(1) binding an AS1411 sequence to S3 of the DNA tetrahedron at the 5' terminal, synthesizing the DNA using an automatic DNA synthesizer to obtain a DNA powder, centrifuging the obtained DNA powder at a high speed to ensure that the DNA powder aggregates at a bottom of the tube, dissolving the obtained DNA powder with $ddH_2O$ (1 nmol DNA is dissolved in 10 μL $ddH_2O$), storing at the condition of 41; wherein the AS1411 sequence is shown in SEQ ID NO: 5, and S3 has a sequence of SEQ ID NO: 3;

(2) measuring an absorbance of the DNA at wavelengths of 260 nm and 330 nm by ultraviolet quantitation method, then calculating the volume of each single strand in a 100 μL, 1 μM system according to the following formula:

$V=100/[(A_{260}-A_{330})\times10^5/(15.2\times a \text{ number of adenine in a single strand}+7.4\times a \text{ number of cytosine in the single strand}+11.4\times a \text{ number of guanine in the single strand}+8.3\times a \text{ number of thymine in the single strand})]$, calculating a total volume of the four single strands according to the above calculation results;

(3) pipetting the DNA obtained in step (1) according to the calculated total volume in step (2), mixing the DNA with a TM buffer (10 mM Tris-HCl, 50 mM $MgCl_2$, pH 8.0) to obtain a mixture, mixing the mixture uniformly with vortex vibration, and putting the mixture into a PCR apparatus; raising the temperature to 95° C. quickly and maintaining for 10 min; and then cooling down to 4° C. and maintaining for 20 min, and finally storing at −20° C. to obtain the nucleic acid aptamer AS1411 modified DNA tetrahedron.

Embodiment 4

A method for preparing a nucleic acid aptamer AS1411 modified DNA tetrahedron includes the following steps:

(1) binding an AS1411 sequence to S4 of the DNA tetrahedron at the 5' terminal, synthesizing the DNA using an automatic DNA synthesizer to obtain a DNA powder, centrifuging the obtained DNA powder at a high speed to ensure that the DNA powder aggregates at a bottom of the tube, dissolving the obtained DNA powder with $ddH_2O$ (1 nmol DNA is dissolved in 10 μL $ddH_2O$), storing at the condition of 4° C.; wherein the AS1411 sequence is shown in SEQ ID NO: 5, and S4 has a sequence of SEQ ID NO: 4;

(2) measuring an absorbance of the DNA at wavelengths of 260 nm and 330 nm by ultraviolet quantitation method, then calculating the volume of each single strand in a 100 μL, 1 μM system according to the following formula:

$V=100/[(A_{260}-A_{330})\times10^5/(15.2\times a \text{ number of adenine in a single strand}+7.4\times a \text{ number of cytosine in the single strand}+11.4\times a \text{ number of guanine in the single strand}+8.3\times a \text{ number of thymine in the single strand})]$, calculating a total volume of the four single strands according to the above calculated results;

(3) pipetting the DNA obtained in step (1) according to the calculated total volume in step (2), mixing the DNA with a TM buffer (10 mM Tris-HCl, 50 mM $MgCl_2$, pH 8.0) to obtain a mixture, mixing the mixture uniformly with vortex vibration, and putting the mixture into a PCR apparatus; raising the temperature to 95° C. quickly and maintaining for 10 min; and then cooling down to 4° C. and maintaining for 20 min, and finally storing at −20° C. to obtain the nucleic acid aptamer AS1411 modified DNA tetrahedron.

Verification of the nucleic acid aptamer AS1411 modified DNA tetrahedrons obtained by the above methods: a polyacrylamide gel electrophoresis (PAGE) method is used. That is, diluting each of the unmodified single strand of the DNA tetrahedron by 100-fold, taking 5 μL of the dilution to mix with 1 μL of 6×loading buffer, taking 5 μL of the modified DNA tetrahedron to mix with 1 μL of 6×loading buffer, adding the solutions into a prepared gel (the ingredients of the gel: ultrapure water 4.2 mL, 40% acrylamide 1.2 mL, 10×TAE 0.6 mL, 10% APS 60 μL, and TEMED 6 μL) respectively, adding a 20 bp marker in a side of the gel as a control, conducting electrophoresis in a 1×TAE buffer at a constant voltage of 100V for 80 minutes. Adding 50 ml $ddH_2O$ and 5 μL Gel-red to a box without light, mixing uniformly, putting the gel into the box, shaking in a shaker for 15-20 minutes, and taking a picture via a gel imaging system. The electrophoretogram is shown in FIGURE.

Embodiment 5

20 mM pH 7.0 sodium phosphate buffer, 150 mM sodium chloride buffer, and 0.5 mM EDTA buffer are taken to prepare the following reaction system: 201M of the nucleic acid aptamer AS1411 modified DNA tetrahedron obtained in Embodiment 4, 4001 μM of Adriamycin, 0.37% vol formaldehyde. The above reaction system is kept at 10° C. to react for 12 h. The obtained product using HPLC, molecular sieve, or ethanol precipitation method (the nucleic acid aptamer AS1411 modified DNA tetrahedron obtained in the present invention binding with drugs is referred as a sample, and the nucleic acid aptamer AS1411 modified DNA tetrahedron obtained without binding drugs is referred as a control) is purified.

The specificity and affinity of the samples against tumor cells are studied by flow cytometry. That is, the samples and the control (200 nM respectively) with tumor cells (A549) are incubated on the ice for half an hour respectively. The substance nonspecifically adsorbed on the cells is washed out with a DPBS buffer. The obtained cells are resuspended in a DPBS (including 5 mM $Mg^{2+}$), and are analyzed using flow cytometry. The result shows that compared with the control, the samples have a specific recognition ability and higher affinity with respect to tumor cells.

Embodiment 6

Plating the cultured tumor cells A549 in 96-well cell culture plates (100 μL, 5×10⁴ cell/well), adding pure Adriamycin or samples with predetermined concentrations (0, 0.1 μM, 0.2 μM, 0.4 μM, 0.8 μM, 1.6 μM, 3.2 μM) into the wells respectively, culturing in a cell incubator for 1.5 h, centrifuging, removing the cell culture medium in the supernatant, adding fresh culture medium to continue culturing for 48 h, then testing the proliferation rate of the cells using a MTS reagent.

The testing result shows that, as the concentration increases, the proliferation rate of tumor cells decreases gradually, indicating that the inhibitory effect of the Adriamycin and samples against tumor cells increases gradually. Compared with the pure Adriamycin, the samples have a stronger inhibitory effect.

---

What is claimed is:

1. A method for preparing a modified DNA tetrahedron modified by a nucleic acid aptamer AS1411, wherein the nucleic acid aptamer AS1411 is a DNA single-strand having a sequence of SEQ ID NO: 5, the method comprises the following steps:

(1) binding the nucleic acid aptamer AS1411 to any one of four DNA single-strands of a DNA tetrahedron at the 5' terminal of the DNA, synthesizing the DNA, dissolving the obtained DNA powder with ddH$_2$O, storing at a condition of 4° C.; wherein the four DNA single strands include a first DNA single-strand having a sequence of SEQ ID NO: 1, a second DNA single-strand having a sequence of SEQ ID NO: 2, a third DNA single-strand having a sequence of SEQ ID NO: 3 and a fourth DNA single-strand having a sequence of SEQ ID NO: 4;

(2) measuring an absorbance of the DNA at wavelengths of 260 nm and 330 nm by ultraviolet quantitation method, then calculating a volume of each single strand in a 100 µL, 1 µM system according to the following formula:

$$V = 100[(A_{260} - A_{330}) \times 10^5 / (15.2 \times \text{a number of adenine in a single strand} + 7.4 \times \text{a number of cytosine in the single strand} + 11.4 \times \text{a number of guanine in the single strand} + 8.3 \times \text{a number of thymine in the single strand})],$$

calculating a total volume of the four single strands according to the above calculated results of each single strand;

(3) pipetting the DNA obtained in step (1) according to the calculated results in step (2), mixing the DNA with a TM buffer to obtain a mixture, mixing the mixture uniformly with vortex vibration, and putting the mixture into a PCR apparatus; raising the temperature to 95° C. and maintaining for 10 min; and then reducing to 4° C. and maintaining for 20 min, and finally storing at −20° C. to obtain the modified DNA tetrahedron modified by the nucleic acid aptamer AS1411.

2. The method of claim 1, wherein in step (1), the DNA powder is dissolved in 10 μL ddH$_2$O.

3. The method of claim 1, wherein the TM buffer in step (3) having a pH value of 8.0 includes 5-10 mM Tris-HCl and 5-50 mM MgCl$_2$.

4. The method of claim 1, wherein the TM buffer in step (3) having a pH value of 8.0 includes 10 mM Tris-HCl and 50 mM MgCl$_2$.

5. A modified DNA tetrahedron modified by a nucleic acid aptamer AS1411, wherein the nucleic acid aptamer AS1411 is a DNA single-strand having a sequence of SEQ ID NO: 5, and the modified DNA tetrahedron is prepared through a method including the following steps:
(1) binding the nucleic acid aptamer AS1411 to any one of the four DNA single-strands of a DNA tetrahedron at the 5' terminal of the DNA, synthesizing the DNA, dissolving the obtained DNA powder with ddH$_2$O, storing at a condition of 4° C.: wherein the four DNA single strands include a first DNA single-strand having a sequence of SEQ ID NO: 1, a second DNA single-strand having a sequence of SEQ ID NO: 2, a third DNA single-strand having a sequence of SEQ ID NO: 3 and a fourth DNA single-strand having a sequence of SEQ ID NO: 4;
(2) measuring an absorbance of the DNA at wavelengths of 260 nm and 330 nm by ultraviolet quantitation method, then calculating a volume of each single strand in a 100 μL, 1 μM system according to the following formula:

$V=100/[(A_{260}-A_{330})\times10^5/(15.2\times a$ number of adenine in a single strand$+7.4\times a$ number of cytosine in the single strand$+11.4\times a$ number of guanine in the single strand$+8.3\times a$ number of thymine in the single strand$)]$, calculating a total volume of the four single strands according to the above calculated results of each single strand;
(3) pipetting the DNA obtained in step (1) according to the calculated results in step (2), mixing the DNA with a TM buffer to obtain a mixture, mixing the mixture uniformly with vortex vibration, and putting the mixture into a PCR apparatus; raising the temperature to 95° C. and maintaining for 10 min; and then reducing to 4° C. and maintaining for 20 min, and finally storing at −20° C. to obtain the modified DNA tetrahedron modified by the nucleic acid aptamer AS1411.

6. The modified DNA tetrahedron of claim 5, wherein in step (1), the DNA powder is dissolved in 10 μL ddH$_2$O.

7. The modified DNA tetrahedron of claim 5, wherein the TM buffer in step (3) having a pH value of 8.0 includes 5-10 mM Tris-HCl and 5-50 mM MgCl$_2$.

8. The modified DNA tetrahedron of claim 5, wherein the TM buffer in step (3) having a pH value of 8.0 includes 10 mM Tris-HCl and 50 mM MgCl$_2$.

* * * * *

SEQUENCE LISTING

<160> NUMBER OF SEQ ID NOS: 9

<210> SEQ ID NO 1
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 1
atttatcacc cgccatagta gacgtatcac caggcagttg agacgaacat tcctaagtct    60
gaa    63

<210> SEQ ID NO 2
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 2
acatgcgagg gtccaatacc gacgattaca gcttgctaca cgattcagac ttaggaatgt    60
tcg    63

<210> SEQ ID NO 3
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 3
actactatgg cgggtgataa aacgtgtagc aagctgtaat cgacgggaag agcatgccca    60
tcc    63

<210> SEQ ID NO 4
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 4
acggtattgg accctcgcat gactcaactg cctggtgata cgaggatggg catgctcttc    60
ccg    63

<210> SEQ ID NO 5
<211> LENGTH: 27
<212> TYPE: DNA
<213> ORGANISM: Artificial Sequence
<220> FEATURE:
<223> OTHER INFORMATION: The sequence is synthesized.

<400> SEQUENCE: 5
ggtggtggtg gttgtggtgg tggtggt    27

<210> SEQ ID NO 6
<211> LENGTH: 90
<212> TYPE: DNA
<213> ORGANISM: Artificial Sequence
<220> FEATURE:
<223> OTHER INFORMATION: The sequence is synthesized.

<400> SEQUENCE: 6
ggtggtggtg gttgtggtgg tggtggtatt tatcacccgc catagtagac gtatcaccag    60
gcagttgaga cgaacattcc taagtctgaa                                     90

<210> SEQ ID NO 7
<211> LENGTH: 90
<212> TYPE: DNA
<213> ORGANISM: Artificial Sequence
<220> FEATURE:
<223> OTHER INFORMATION: The sequence is synthesized.

<400> SEQUENCE: 7
ggtggtggtg gttgtggtgg tggtggtaca tgcgagggtc caataccgac gattacagct    60
tgctacacga ttcagactta ggaatgttcg                                     90

<210> SEQ ID NO 8
<211> LENGTH: 90
<212> TYPE: DNA
<213> ORGANISM: Artificial Sequence
<220> FEATURE:
<223> OTHER INFORMATION: The sequence is synthesized.

<400> SEQUENCE: 8
ggtggtggtg gttgtggtgg tggtggtact actatggcgg gtgataaaac gtgtagcaag    60
ctgtaatcga cgggaagagc atgcccatcc                                     90

<210> SEQ ID NO 9
<211> LENGTH: 90
<212> TYPE: DNA
<213> ORGANISM: Artificial Sequence
<220> FEATURE:
<223> OTHER INFORMATION: The sequence is synthesized.

<400> SEQUENCE: 9
ggtggtggtg gttgtggtgg tggtggtacg gtattggacc ctcgcatgac tcaactgcct    60
ggtgatacga ggatgggcat gctcttcccg                                     90